(12) United States Patent
Mao

(10) Patent No.: US 6,930,191 B2
(45) Date of Patent: Aug. 16, 2005

(54) METHODS OF PREPARING TOCOPHEROL COMPOUND SALTS IN SUPERCRITICAL MEDIA

(75) Inventor: Jianhua Mao, West Chester, OH (US)

(73) Assignee: Cognis Corporation, Ambler, PA (US)

(*) Notice: Subject to any disclaimer, the term of this patent is extended or adjusted under 35 U.S.C. 154(b) by 0 days.

(21) Appl. No.: 10/681,477

(22) Filed: Oct. 8, 2003

(65) Prior Publication Data

US 2004/0138478 A1 Jul. 15, 2004

Related U.S. Application Data

(60) Provisional application No. 60/417,685, filed on Oct. 10, 2002.

(51) Int. Cl.$^7$ .................................................. C07D 311/72
(52) U.S. Cl. ........................................ 549/410; 549/412
(58) Field of Search ................................. 549/410, 412

(56) References Cited

U.S. PATENT DOCUMENTS

| | | | |
|---|---|---|---|
| 3,432,525 A | 3/1969 | Kijima et al. | |
| 6,426,391 B1 | 7/2002 | DeSimone et al. | |
| 6,452,023 B1 | 9/2002 | Aquino et al. | |

*Primary Examiner*—Taofiq Solola
(74) *Attorney, Agent, or Firm*—John F. Daniels

(57) ABSTRACT

Methods for preparing salts of tocopherol dibasic acid hemiesters in supercritical media are described.

9 Claims, No Drawings

METHODS OF PREPARING TOCOPHEROL COMPOUND SALTS IN SUPERCRITICAL MEDIA

CROSS-REFERENCE TO RELATED APPLICATIONS

This application claims priority, under 35 U.S.C. §119(e), of U.S. Provisional Patent Application No. 60/417,685, filed on Oct. 10, 2002, the entire contents of which are hereby incorporated by reference.

BACKGROUND OF THE INVENTION

Concerns over maintaining good health continue to grow, and accordingly, vitamin and antioxidant use and intake also continue to rise. As more evidence of the potential benefits associated with the use and intake of vitamins and antioxidants continues to be generated, demand for such substances increases, as does the demand for various forms thereof. Many naturally derived antioxidants and vitamins are normally delivered as oily substances or viscous liquids for encapsulation. However, many potential applications for increased, beneficial consumption and use of such vitamins and antioxidants make solid, free-flowing, and/or powdery formulations more desirable.

For example, tocopherol compounds, which exhibit vitamin E activity, can be made into solids in the form of esters. D-alpha-tocopherol is an oily liquid. Unfortunately, solid forms of tocopherol such as tocopherol acetate and tocopherol succinate still do not adequately meet all of the applicational demands necessitated by the various forms of desired vitamin consumption, including, for example, compaction for tableting. Tocopherol compound salts, namely salts of dibasic acid hemiesters of tocopherol, provide tocopherol compounds that exhibit favorable formulation properties. One specific example of such a salt is the calcium salt of tocopherol succinate. However, existing methods for producing such salts from dibasic acid hemiester and calcium starting materials are costly, complicated, and/or inefficient, and thus not widely employed to produce such compounds for use in the vitamin market.

Known processes for producing tocopherol calcium succinate include two step processes wherein a starting material such as tocopherol succinic acid is reacted with lithium hydroxide to produce the lithium salt of tocopherol succinate, which is then reacted with a calcium compound to exchange the lithium ion with a calcium ion. Other processes react tocopherol succinic acid with calcium salts in aqueous methanol to attempt to achieve adequate reaction, but separation of the product is less than ideal and the reaction is slow.

Thus, there is a need in the art for a process by which tocopherol calcium succinate and other beneficial tocopherol compound salts can be prepared in high yield both quickly and cost-effectively.

BRIEF SUMMARY OF THE INVENTION

The present invention is directed to methods for preparing salts of dibasic acid hemiesters of tocopherol compounds. More specifically, the present invention is directed to methods of reacting a tocopherol starting material with a salt reagent in various supercritical fluid media to produce a salt of a dibasic acid hemiester of a tocopherol compound. The methods according to the present invention provide products in high yield both efficiently and rapidly.

One embodiment of the present invention includes a method of preparing a divalent metal salt of a tocopherol dibasic acid hemiester, which comprises: (a) providing (i) a tocopherol dibasic acid hemiester starting material and (ii) a divalent metal salt; and (b) reacting the tocopherol dibasic acid hemiester starting material and the divalent metal salt in a supercritical fluid medium. In preferred embodiments, the tocopherol dibasic acid hemiester starting material includes a tocopherol succinate starting material and the divalent metal salt is a calcium salt.

In other preferred embodiments of the present invention the tocopherol succinate starting material comprises tocopherol succinic acid, and the calcium salt comprises one or more inexpensive, common calcium salts having little or no water solubility, including but not limited to CaO, $Ca(OH)_2$, and $CaCO_3$.

The processes in accordance with the present invention are preferably used to react a tocopherol succinate starting compound and a calcium salt which are not equally soluble in the same solvent under the conventional conditions. The processes employ a supercritical fluid as a reaction medium, the supercritical fluid being maintained at conditions of temperature and pressure such that the solubility of both the tocopherol dibasic acid hemiester starting material and the salt reagent are sufficiently high that a reaction between the two is rapid and efficient.

DETAILED DESCRIPTION OF THE INVENTION

Tocopherol dibasic acid hemiester starting materials which are useful in the processes according to the present invention are based upon dibasic acid hemiesters of one or more tocopherol compounds. As used herein, the term "tocopherol compounds" refers to the broad class of compounds that can be characterized as derivatives of 6-chromanol having an isoprenoid side chain, of which many are known to exhibit vitamin E activity. These compounds include, for example, the alpha ($\alpha$-), beta ($\beta$-), gamma ($\gamma$-) and delta ($\delta$-) homologues of tocopherol, as well as unsaturated derivatives, such as, tocomonoenols, tocodienols and tocotrienols. The tocopherol dibasic acid hemiester starting materials which are useful in the processes according to the present invention may be synthetic or naturally-derived, and may include either optical enantiomer of any of the aforementioned homologues, or mixtures thereof. In preferred embodiments of the present invention, naturally-derived tocopherol starting materials are used. Preferably the tocopherol starting materials used in the processes according to the present invention include d-$\alpha$-tocopherol compounds, most preferably d-$\alpha$-tocopherol succinic acid. Mixtures of naturally-derived tocopherols may also be used, such as, for example, mixtures of alpha ($\alpha$-), beta ($\beta$-), gamma ($\gamma$-) and/or delta ($\delta$-) tocopherol.

Dibasic acid components useful for preparing the dibasic acid hemiesters used as tocopherol starting materials in the processes of the present invention include $C_2$–$C_{12}$ dicarboxylic acids. The dicarboxylic acids may be straight or branched, saturated or unsaturated. The acids may be substituted with, for example, an $\alpha$-hydroxy moiety. Examples of suitable dicarboxylic acids for use in preparing the dibasic acid hemiesters used as tocopherol starting materials in the processes of the present invention include malonic acid, succinic acid, pentadienoic acid, hexadienoic acid, heptadienoic acid, maleic acid, fumaric acid, azelaic acid, dodecanedioic acid. The preferred dibasic acid component for use in preparing the dibasic acid hemiesters is succinic acid.

The dibasic acid hemiesters used as tocopherol starting materials in the processes of the present invention can be obtained commercially from various sources such as Cognis Corporation, available as Covitol® 1210 natural d-α-tocopherol succinic acid, but may also be prepared by reacting one or more tocopherol compounds and a dibasic component selected from dibasic acids, dibasic acid anhydrides, and dibasic acid halides. Methods of preparing the dibasic acid hemiesters are known and include any known preparative method for esterifying a tocopherol compound and an acid, such as direct esterification and transesterification using suitable catalysts. A preferred route for preparing tocopherol succinic acid for use in the present invention is the direct esterification of d-α-tocopherol with succinic anhydride.

The dibasic acid hemiester of a tocopherol compound is preferably reacted with one or more divalent metal salts, including, for example, salts of calcium, magnesium, zinc, to form a tocopherol salt product. More preferred embodiments include the use of calcium salt reagents. The particular calcium salt(s) used in the method according to the present invention can vary widely and is not critical per se. Accordingly, any calcium salt can be used. However, the method according to the present invention is preferably used to react a dibasic acid hemiester and one or more commonly available, inexpensive calcium salts which does not exhibit adequate solubility in water or common organic solvents, such as methanol, other alcohols, acetone, hexane, ethers and/or esters at standard temperature and pressure conditions. Such calcium salts include CaO, $Ca(OH)_2$ and $CaCO_3$. Other calcium salts which exhibit moderate water solubility, but which can be used nonetheless include, but are not limited to, calcium acetate, calcium proprionate, calcium nitrate, calcium sulfate, calcium chloride and calcium phosphate. In the most preferred embodiments of the present invention the calcium reagent comprises CaO, $Ca(OH)_2$ and/or $CaCO_3$. All of the calcium reagents useful in the present invention are commercially available from a number of sources including distributors such as Sigma and Aldrich.

The methods according to the present invention are carried out using a supercritical fluid as the reaction medium. In preferred embodiments of the present invention, the advantageous solubility properties provided by supercritical fluid media make it possible to efficiently and rapidly react reagents which are not otherwise jointly soluble in standard systems, either aqueous or non-aqueous. In other embodiments, supercritical fluid media may be employed despite the co-solubility of both the tocopherol starting material and the calcium reagent to provide higher efficiency and ease of product recovery.

Supercritical fluid is a term which refers to matter which is in a state above its critical point. The critical point for any compound or element is the set of temperature and pressure conditions above which the compound or element exhibits liquid and gas properties. Above its critical point, a medium, i.e., a supercritical fluid, cannot be liquefied by the application of pressure or elevation of temperature. A gas in the supercritical state is referred to as a supercritical fluid. Supercritical fluids have high solvating capabilities that are typically associated with compositions in the liquid state. Supercritical fluids also have a low viscosity that is characteristic of compositions in the gaseous state. Furthermore, supercritical fluids are able to penetrate (i.e., effectively contact) surfaces better than compositions in the liquid state.

Many different compounds and elements can be employed as the reaction medium for use in the processes according to the present invention including, but not limited to, carbon dioxide, water, benzene, toluene, gases such as nitrogen, helium, neon, argon, krypton, xenon, and other inert components, or mixtures thereof. Every compound or element has its own critical point. For example, carbon dioxide reaches its critical point at a temperature of about 31° C. and a pressure of about 73 atm. Water reaches its critical point at a temperature of about 375° C. and a pressure of about 227 atm. In view of the much higher temperatures and pressures associated with water's critical point, and given the prevalence of carbon dioxide, $CO_2$ is the preferred choice of reaction medium. The reaction according to the methods of the present invention can be carried out at any set of temperature and pressure conditions sufficient to render the reaction medium supercritical. Preferably, the reaction medium comprises carbon dioxide and the temperature is from about 30° C. (i.e., equivalent to or greater than the critical temperature) to about 400° C., and the pressure during the reaction is from about 70 atm (i.e., equivalent to or greater than the critical pressure) to about 600 atm.

The supercritical reaction media useful in the method according to the present invention may also include modifiers. Modifiers are added components that alter the polarity and/or solubility of the main component of the medium. Typical modifiers include alcohols and hydrocarbons. Suitable modifiers include lower alkanols such as methanol, ethanol, isopropanol, as well as hydrocarbons such as hexane, cyclohexane, benzene, toluene, xylene, tetrahydrofuran, and diethyl ether. Typically, the modifier is present in an amount of up to 10% by weight of the medium. In preferred embodiments according to the present invention, the reaction medium comprises from about 0.1 to about 5% by weight of one or more modifiers. The most preferred modifiers include the lower alkanols.

The reaction in accordance with the present invention can be carried out in any reactor suitable for the necessary temperature and pressure. High pressure reaction vessels are commercially available.

The tocopherol starting material and the calcium reagent of the present invention are generally reacted in a molar ratio of at least about 2:1. Although excess is not required for suitable yield, a slight excess or a slight undercharge may be employed if desired to ensure completion. The typical residence time necessary for the reagents can vary depending on the operating temperature and pressure. In general, the higher the temperature and pressure, the shorter the residence time for the reagents in the reactor. Typically, at a temperature of about 100° C. and a pressure of about 400 atm, a residence time of about 4 hours will suffice for the reaction to be complete.

In one preferred embodiment of the present invention, a tocopherol starting material comprising d-α-tocopherol succinic acid is reacted with calcium carbonate, at a molar ratio of 2:1, in supercritical carbon dioxide at a temperature of at least about 50° C. and a pressure of at least about 100 atm for a period of at least a half an hour.

After the reaction is complete, the reactor is cooled, preferably to from about 30° C. to about 60° C. The solvent, e.g., $CO_2$, is removed by releasing the gas. The product is left in the reactor after the gas is released. The product can be dried, preferably under vacuum at a temperature of from about 50° C. to about 60° C. for about 4 hours. If a modifier or solvent which is liquid at room temperature is employed, drying may be necessary. Large scale drying processes, such as spray-drying, freeze-drying, etc. can be utilized.

The present invention will now be illustrated in more detail by reference to the following specific, non-limiting examples.

EXAMPLE 1

To a 1 liter high pressure reactor equipped with temperature control and mechanical stirring, approximately 53 g (0.1 moles) of d-α-tocopherol succinic acid are added in addition to approximately 5 g (0.05 moles) of calcium carbonate. The reactor is closed, charged with $CO_2$, and brought to a temperature of about 120° C. and a pressure of about 300 atm. The reaction system is held at these conditions and stirred for about 60 minutes. The reactor temperature is then lowered, the $CO_2$ is removed and the product is removed and dried.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of preparing a salt of a tocopherol dibasic acid hemiester, said method comprising:
   (a) providing (i) a tocopherol dibasic acid hemiester starting material and (ii) a divalent metal salt; and
   (b) reacting the tocopherol dibasic acid hemiester starting material and the divalent metal salt in a supercritical fluid medium.

2. The method according to claim 1, wherein the tocopherol dibasic acid hemiester starting material comprises tocopherol succinic acid.

3. The method according to claim 1, wherein the divalent metal salt comprises a calcium salt reagent.

4. The method according to claim 1, wherein the divalent metal salt comprises a component selected from the group consisting of CaO, $Ca(OH)_2$ and $CaCO_3$.

5. The method according to claim 1, wherein the supercritical fluid medium comprises $CO_2$.

6. The method according to claim 5, wherein the supercritical fluid medium is held at a temperature of from about 30° C. to about 400° C. and a pressure of from about 60 bar to about 800 bar during the reaction.

7. The method according to claim 5, wherein the supercritical fluid medium further comprises one or more modifiers.

8. The method according to claim 7, wherein the one or more modifiers is present in an amount of from about 0.01 to about 10% by weight.

9. The method according to claim 7, wherein the one or more modifiers is selected from the group consisting of methanol, ethanol, isopropanol, cyclohexane, benzene, toluene, xylene, ethers, tetrahydrofuran and mixtures thereof.

* * * * *